(12) United States Patent
Chelak et al.

(10) Patent No.: US 10,226,613 B2
(45) Date of Patent: Mar. 12, 2019

(54) MULTI-PURPOSE PROTECTIVE COVERING FOR USE ON A MEDICAL DEVICE

(71) Applicant: NP Medical Inc., Clinton, MA (US)

(72) Inventors: Todd M. Chelak, Westborough, MA (US); Ian Kimball, Townsend, MA (US); Luis Maseda, Natick, MA (US); Paul Zeytoonian, Sudbury, MA (US)

(73) Assignee: NP Medical Inc., Clinton, MA (US)

( * ) Notice: Subject to any disclaimer, the term of this patent is extended or adjusted under 35 U.S.C. 154(b) by 906 days.

(21) Appl. No.: 14/460,596

(22) Filed: Aug. 15, 2014

(65) Prior Publication Data

US 2014/0358115 A1 Dec. 4, 2014

Related U.S. Application Data

(63) Continuation of application No. PCT/US2013/026155, filed on Feb. 14, 2013.

(60) Provisional application No. 61/598,956, filed on Feb. 15, 2012.

(51) Int. Cl.
*A61M 39/20* (2006.01)
*A61M 5/14* (2006.01)
*A61M 39/16* (2006.01)

(52) U.S. Cl.
CPC .......... *A61M 39/20* (2013.01); *A61M 5/1418* (2013.01); *A61M 39/162* (2013.01); *A61M 2205/0205* (2013.01)

(58) Field of Classification Search
CPC .................................................... A61M 39/20
See application file for complete search history.

(56) References Cited

U.S. PATENT DOCUMENTS

| | | | |
|---|---|---|---|
| 4,432,764 A | 2/1984 | Lopez | 604/283 |
| 4,440,207 A | 4/1984 | Genatempo et al. | 150/52 R |
| 4,624,664 A | 11/1986 | Peluso et al. | 604/256 |
| 4,655,762 A | 4/1987 | Rogers | 604/403 |
| 4,810,241 A | 3/1989 | Rogers | 604/28 |
| 5,242,425 A | 9/1993 | White et al. | 604/256 |

(Continued)

FOREIGN PATENT DOCUMENTS

| | | | | |
|---|---|---|---|---|
| EP | 1 430 923 A2 | 6/2004 | | A61M 16/04 |
| WO | WO 97/26932 A1 | 7/1997 | | A61M 5/00 |

OTHER PUBLICATIONS

Heiko Krassow, Authorized officeer European Patent Office, International Search Report—Application No. PCT/US2013/026155, dated Sep. 19, 2013, 17 pages, together with the Written Opinion of the International Searching Authority.

*Primary Examiner* — Nathan R Price
*Assistant Examiner* — Tasnim Mehjabin Ahmed
(74) *Attorney, Agent, or Firm* — McCarter & English, LLP; Jonathan C. Lovely

(57) ABSTRACT

A multi-purpose covering for use with a medical device having a housing and an access port includes a substrate with a first end and a second end. The substrate defines the structure of the covering. The covering also includes a first securing portion nearer the first end of the substrate for securing at least one protective cap to the substrate, and a second securing portion nearer the second end for securing the substrate to the medical device. To protect the access port when the covering is sealed to the medical device, the covering can also include a sealing portion configured to be releasably secured to the medical device.

15 Claims, 13 Drawing Sheets

(56) References Cited

U.S. PATENT DOCUMENTS

| | | | | |
|---|---|---|---|---|
| 5,554,135 | A | 9/1996 | Menyhay | 604/256 |
| 5,792,120 | A | 8/1998 | Menyhay | 604/256 |
| 6,003,556 | A | 12/1999 | Brugger et al. | 138/89 |
| 6,045,539 | A | 4/2000 | Menyhay | 604/256 |
| 6,911,025 | B2 | 6/2005 | Miyahara | 604/415 |
| 7,083,605 | B2 | 8/2006 | Miyahara | 604/415 |
| 7,198,611 | B2 | 4/2007 | Connell et al. | 604/30 |
| 7,452,349 | B2 | 11/2008 | Miyahara | 604/415 |
| 8,075,530 | B2 * | 12/2011 | Taylor | A61B 17/3462 604/167.01 |
| 2004/0236311 | A1 | 11/2004 | Ishii et al. | 604/533 |
| 2007/0112333 | A1 | 5/2007 | Hoang et al. | 604/533 |
| 2008/0019889 | A1 | 1/2008 | Rogers et al. | 422/292 |
| 2009/0149819 | A1 | 6/2009 | Chelak | 604/246 |
| 2012/0016318 | A1 | 1/2012 | Hoang et al. | 604/288.01 |
| 2012/0216359 | A1 * | 8/2012 | Rogers | B08B 1/00 15/104.93 |
| 2012/0220955 | A1 * | 8/2012 | Maseda | A61M 39/16 604/256 |
| 2013/0199947 | A1 * | 8/2013 | Tennican | A61B 19/0256 206/216 |

\* cited by examiner

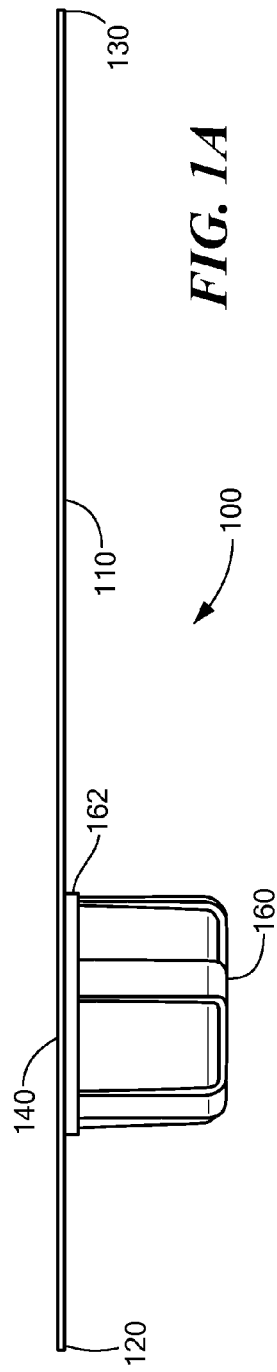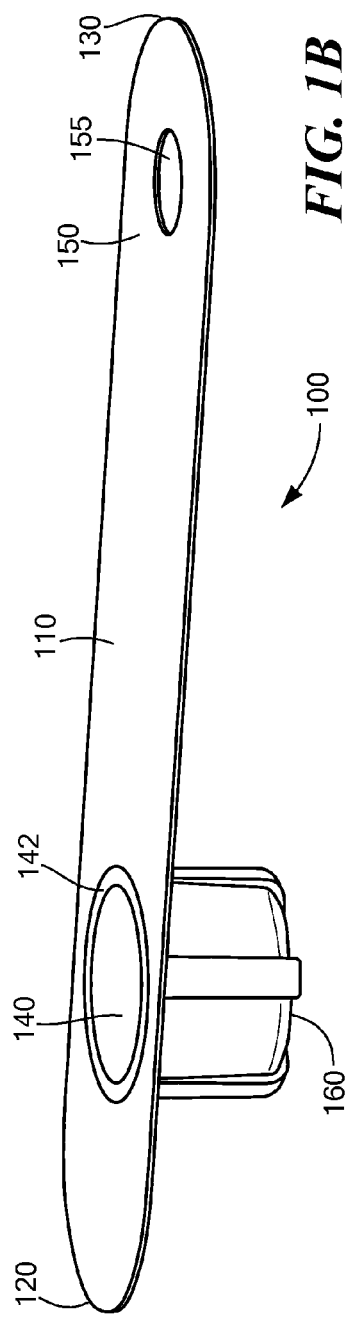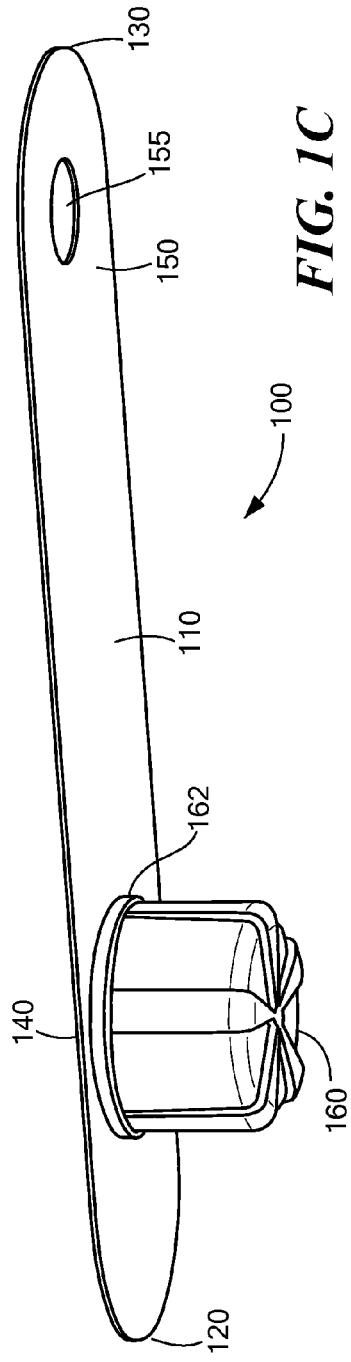

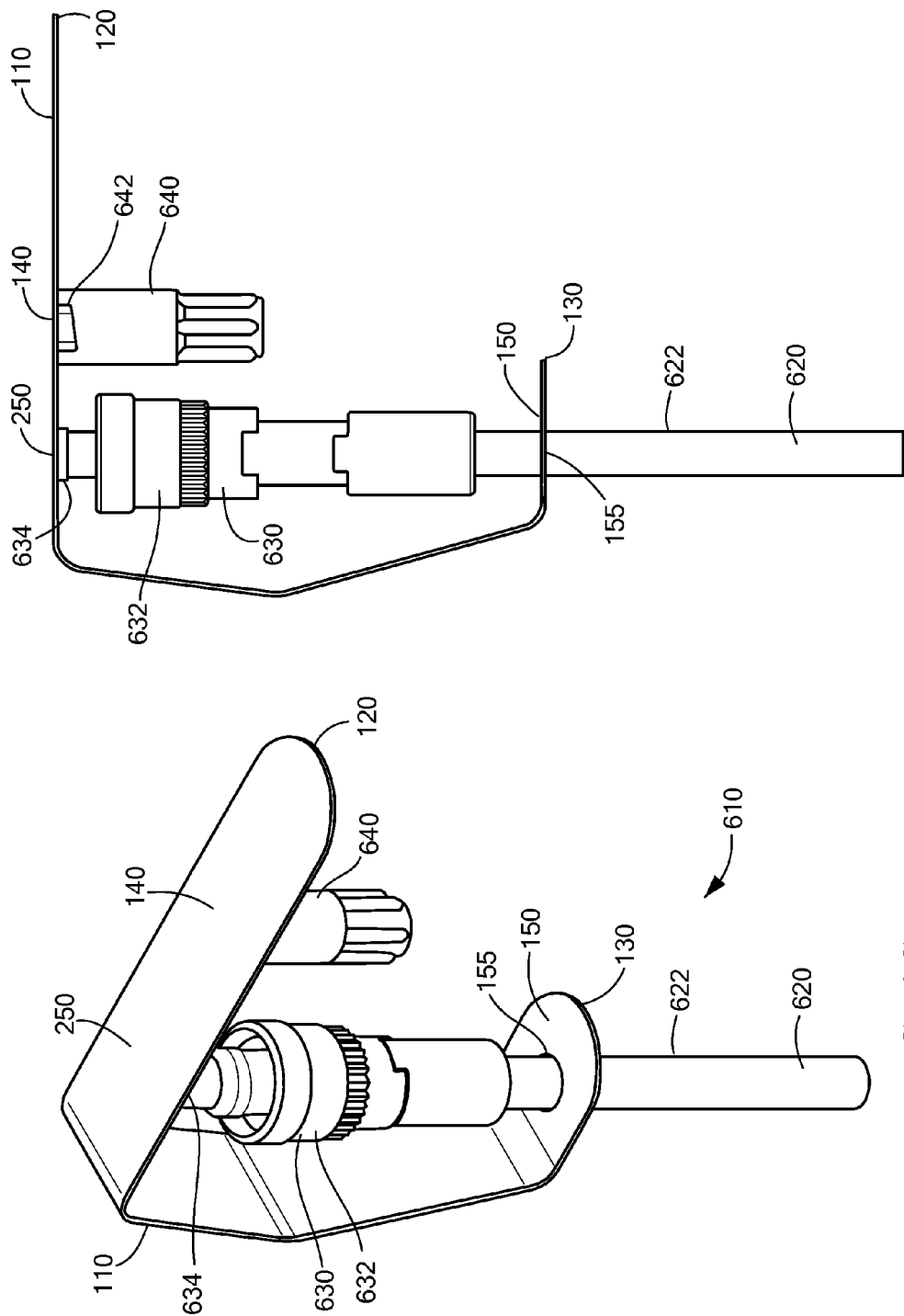

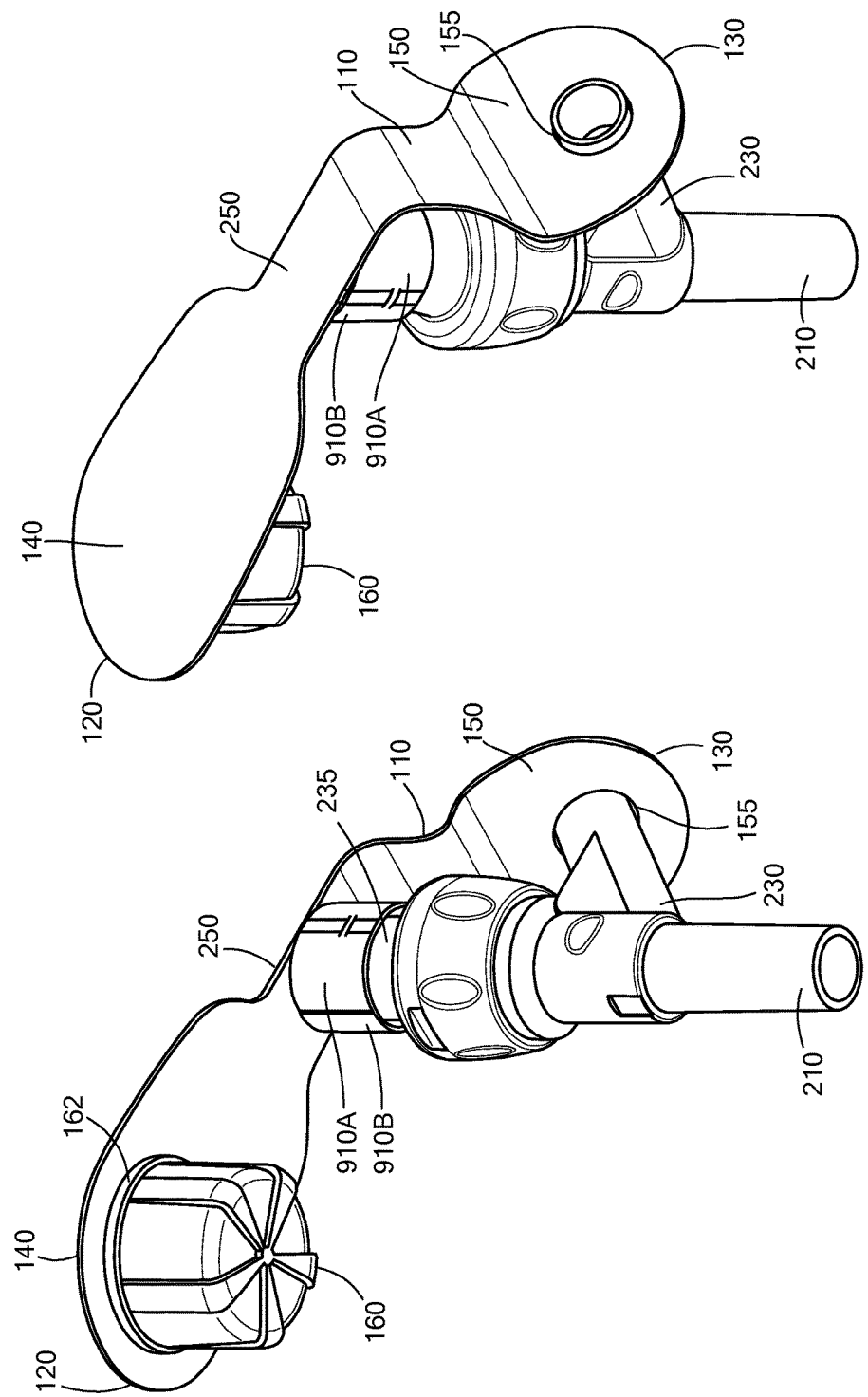

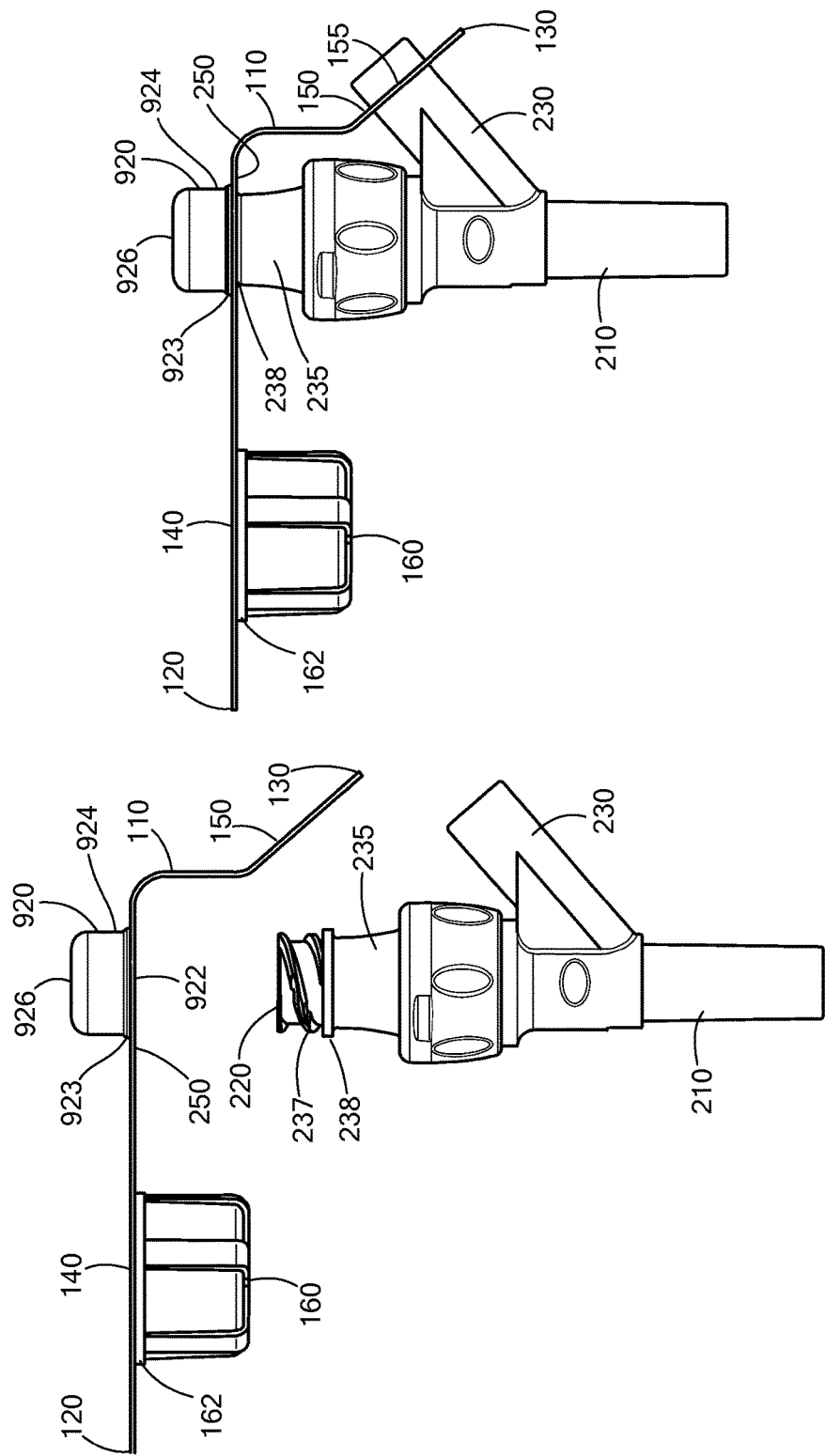

MULTI-PURPOSE PROTECTIVE COVERING FOR USE ON A MEDICAL DEVICE

PRIORITY

This application is a continuation of co-pending Patent Cooperation Treaty application PCT/US2013/026155, entitled "Multi-Purpose Protective Covering for use on a Medical Device," filed Feb. 14, 2013, and naming Todd Chelak, Ian Kimball, Luis Maseda, and Paul Zeytoonian as inventors, the disclosure of which is incorporated herein, in its entirety, by reference.

Patent Cooperation Treaty application PCT/US2013/026155, in turn, claims priority from U.S. Provisional Patent Application No. 61/598,956, filed Feb. 15, 2012, entitled, "Multi-Purpose Protective Covering for Use on a Medical Device," and naming Todd Chelak, Ian Kimball, Luis Maseda, and Paul Zeytoonian as inventors, the disclosure of which is incorporated herein, in its entirety, by reference.

FIELD OF THE INVENTION

The invention generally relates to cleaning devices and, more particularly, the invention relates to protective coverings and caps for protecting and cleaning medical device access ports.

BACKGROUND OF THE INVENTION

Standard institutional practice typically requires the top of a medical valve (or other medical device IV access ports) to be cleaned/swabbed prior to each access, such as prior to insertion of a syringe into the medical valve. The proper technique for cleaning medical device access ports requires attention, diligence and a small amount of time. It is critical that the access port is properly cleaned prior to each access. If the access port is not properly cleaned, microbes may be pushed into the medical device and enter the blood stream, which may cause serious infection (e.g., Catheter Related Blood Stream Infections or "CRBSI").

Several factors may lead to a medical device access port not being properly cleaned or protected. In many cases, the swabbing technique is inadequate due to lack of awareness. In other cases the access port top geometry contains features that trap debris and microbes that inhibit adequate cleaning and removal. Additionally, there are instances in which the access port does not get cleaned at all due to the many distractions that may be taking place, haste, or lack of disinfecting supplies available at the instance the medical device is to be used. Furthermore, the medical device may be exposed to debris and microbes for a period of time prior to first use, making cleaning more difficult.

The most common way of cleaning and disinfecting an IV access port is to use a single-use alcohol wipe (70% IPA). These wipes (pads) are commonly found throughout the institution packaged in foil pouches/packets, one per packet. Once removed from the packet, a user may grasp the wipe with their forefinger and thumb and swipe it across the top of the access port.

There are numerous problems associated with this method of cleaning a medical device. First, a single swipe may be insufficient to adequately clean the access port. Additionally, the alcohol wipe may be unable to clean in crevices and grooves in the access port.

Another way of cleaning and disinfecting a medical device is to use a swab cap. As the name suggests, swab caps are caps that may be placed over the medical device and used to swab the access port. Each swab cap may include a swab material pre-loaded with a cleaning agent (e.g. 70% IPA) within the interior of the cap. When the cap is placed over the access port of the medical device housing, the swab material contacts the access port, and the cleaning agent cleans/disinfects the access port. Problems associated with such caps are that they may not be readily available (e.g., the medical staff may not be near the supply of caps when needed), and they are easily lost/misplaced.

Additionally, swab caps do not protect the access port upon the medical device's removal from a primary, sterile package. Furthermore, swab caps are typically not used until after the initial access of the medical device, which may be hours to days after the medical device is removed from the sterile package.

SUMMARY OF THE INVENTION

In accordance with one embodiment of the invention, a multi-purpose covering for use with a medical device having a housing and an access port includes a substrate with a first end and a second end, and defining the structure of the covering. The covering may also include (1) a first securing portion nearer the first end of the substrate for securing at least one protective cap (e.g., at least one medical valve protective cap and/or at least one male luer protective cap) to the substrate, and (2) a second securing portion nearer the second end for securing the substrate to the medical device. To maintain the sterility of the access port when the protective covering is sealed to the medical device (e.g., prior to first use of the medical device), the covering may also include a sealing portion configured to be releasably secured to the medical device.

In some embodiments, the covering may include an antimicrobial coating, and the sealing portion may be located between the first securing portion and the second securing portion. The first securing portion may have an adhesive to secure the substrate to the protective cap(s), and/or the first securing portion may be bonded to the protective cap(s). Similarly, the sealing portion may include an adhesive for sealing the sealing portion to the medical device, and/or the sealing portion may be bonded or welded to the medical device.

The second securing portion may include a through hole passing through the substrate. The through hole may fit over at least a portion of the medical device to secure the substrate to the medical device. Alternatively, the second securing portion may be bonded to a portion of the medical device. For example, the medical device may be a medical valve with an inlet housing, and the second securing portion may be bonded to the inlet housing. Additionally or alternatively, the second securing portion may include an adhesive that secures the substrate to the medical device.

In further embodiments, the substrate may include perforations. The perforations may be located between the second securing portion and an edge of the substrate, and/or between the second securing portion and the sealing portion. The protective cap(s) may contain a swab material pre-loaded with a cleaning agent. The sealing portion may include a hydrophobic filter element that allows air from the medical device to pass through the covering, and prevents bacteria from entering the medical device.

In some embodiments, the covering may also include at least one tab extending outward from the sealing portion. The tab(s) may be folded towards the medical device and wrapped around a portion of the housing of the medical device. For example, if the medical device is a medical valve having an inlet housing, the tab(s) may wrap around the inlet housing to cover threads located on the inlet housing.

Additionally or alternatively, the sealing portion may include a pocket with an annular side wall extending proximally from the sealing portion and a top surface. The pocket may be configured to fit over at least a portion of the housing. For example, if the medical device is a medical valve with an inlet housing, the pocket may fit over at least a portion of the inlet housing to cover the threads located on the inlet housing. The sealing portion may be located at a base of the annular side wall, and may seal against the inlet housing of the medical valve.

In accordance with additional embodiments, a medical device may include a housing forming an interior, an access port, and a protective covering. The protective covering may, in turn, include (1) a substrate having a first end and a second end and defining the structure of the covering, (2) a first securing portion nearer the first end of the substrate for securing at least one protective cap to the substrate, (3) a second securing portion nearer the second end and secured to the medical device, and (4) a sealing portion releasably secured to the medical device. The sealing portion may maintain the sterility of the access port when sealed to the housing and prior to first use of the medical device. The protective covering may also include an antimicrobial coating.

The sealing portion may be located between the first securing portion and the second securing portion. The first securing portion may have an adhesive that secures the substrate to the protective cap(s), and/or the first securing portion may be bonded to the protective cap(s). The sealing portion may include an adhesive that seals the sealing portion to the housing, and/or the sealing portion may be bonded or welded to the housing.

The second securing portion may include a through hole passing through the substrate. The through hole may fit over at least a portion of the housing to secure the substrate to the housing. Alternatively, the second securing portion may be bonded or welded to the housing, and may include an adhesive that secures the substrate to the housing. The substrate may also include perforations located between the second securing portion and an edge of the substrate, and/or between the second securing portion and the sealing portion.

The protective cap(s) may include a medical valve protective cap and/or a male Luer protective cap, and may contain a swab material pre-loaded with a cleaning agent. The sealing portion may include a hydrophobic filter element that allows air from the medical device to pass and prevents bacteria from entering the medical device.

In additional embodiments, the covering may include at least one tab extending from the sealing portion and wrapped around a portion of the housing. The medical device may be a medical valve with an inlet housing having threads, and the tab(s) may wrap around the inlet housing to cover the threads. Additionally or alternatively, the sealing portion may include a pocket with an annular side wall extending proximally from the sealing portion, and a top surface. The pocket may fit over and cover a portion of the housing (e.g., the inlet housing such that the pocket covers the threads). The sealing portion may be located at a base of the annular wall and seal against a side of the inlet housing.

In accordance with further embodiments, a method for maintaining the sterility of a medical device includes providing a medical device and a protective covering. The medical device may have a housing forming an interior, and an access port. The protective covering may include (1) a substrate having a first end and a second end and defining the structure of the covering, (2) a first securing portion nearer the first end of the substrate, (3) at least one protective cap secured to the first securing portion, (4) a second securing portion nearer the second end, and (5) a sealing portion. The method may also include securing the second securing portion to the medical device to secure the substrate to the medical device, and releasably securing the sealing portion to the medical device. The sealing portion may maintain the sterility of the access port when sealed to the medical device, and prior to first use of the medical device.

The method may also include removing the sealing portion from the medical device, connecting the medical device to a second medical device, and transferring fluid through the medical device and the second medical device. After transferring the fluid, the method may then disconnect the second medical device from the medical device, remove a first protective cap from the first securing portion, and secure the first protective cap to the access port. The method may also include removing a second protective cap from the securing portion, and securing the second protective cap to the second medical device.

In some embodiments, the protective covering may further include an antimicrobial coating, and the first securing portion may have an adhesive to secure the substrate to the protective cap(s). Alternatively, the first securing portion may be bonded to the protective cap(s). The sealing portion may include an adhesive for releasably securing the sealing portion to the medical device, and releasably securing the sealing portion to the medical device may include bonding the sealing portion to the medical device.

The second securing portion may include a through hole passing through the substrate, and securing the second securing portion to the medical device may include fitting the through hole over at least a portion of the medical device. Alternatively, securing the second securing portion may include bonding the second securing portion to at least a portion of the medical device. In some embodiments, the second securing portion may include an adhesive that secures the substrate to the medical device.

The covering may include at least one tab extending from the sealing portion, and releasably securing the sealing portion to the medical device may include folding the tab(s) towards the medical device and wrapping the tab(s) around a portion of the housing. The medical device may be a medical valve with an inlet housing, and the tab(s) may wrap around the inlet housing and cover threads located on the inlet housing. Additionally or alternatively, the sealing portion may include a pocket having an annular wall extending proximally from the sealing portion, and a top surface. Releasably securing the sealing portion may include fitting the pocket over a portion of the housing. The sealing portion may be located at a base of the annular wall, and may seal against the housing.

BRIEF DESCRIPTION OF THE DRAWINGS

The foregoing advantages of the invention will be appreciated more fully from the following further description thereof with reference to the accompanying drawings wherein:

FIGS. 1A-1C schematically show a multi-purpose protective covering, in accordance with various embodiments of the present invention.

FIGS. 6A-6C schematically show a further embodiment of a multi-purpose protective covering for a male Luer connector, in accordance with some embodiments of the present invention.

FIGS. 7A-7C schematically show an alternative embodiment of a multi-purpose protective covering having a filter member, in accordance with further embodiments of the present invention.

FIGS. 9A-9C schematically show an alternative embodiment of a multi-purpose protective covering, in accordance with additional embodiments of the present invention.

FIGS. 10A-10C schematically show an alternative embodiment of a multi-purpose protective covering having a pocket formed in the protective covering, in accordance with embodiments of the present invention.

DESCRIPTION OF ILLUSTRATIVE EMBODIMENTS

Figure 2A:
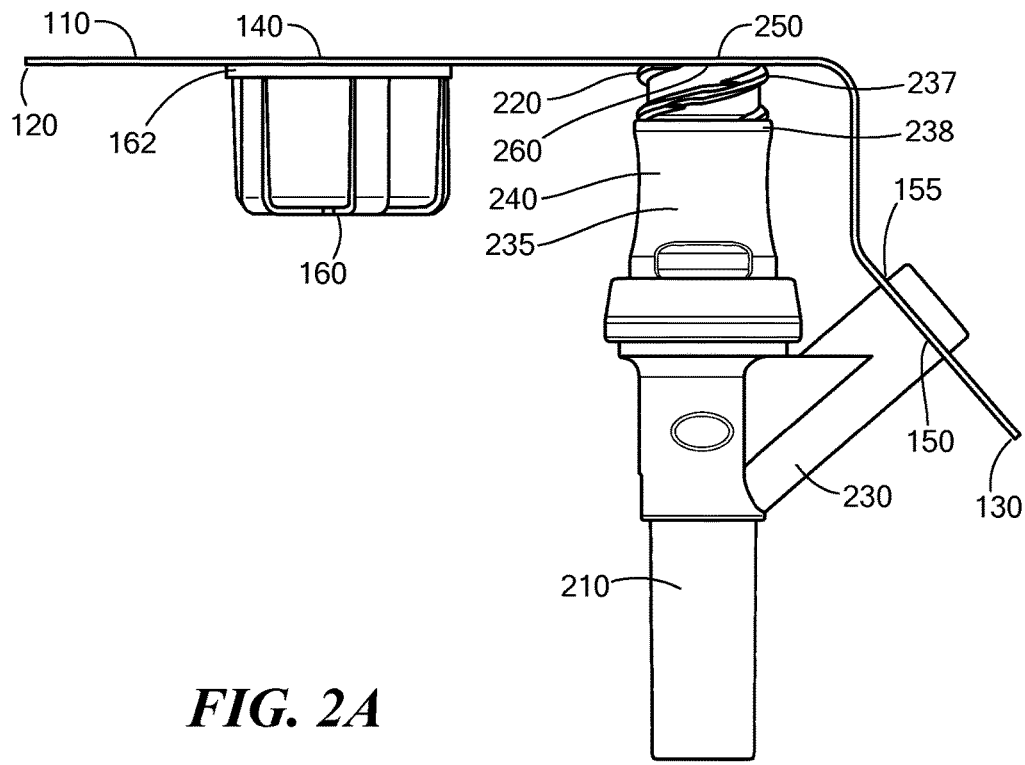
FIGS. 2A-2B schematically show the multi-purpose protective covering shown in FIGS. 1A-1C secured to a medical valve in accordance with some embodiments of the present invention.

In illustrative embodiments, a multi-purpose protective covering may be used to (1) provide a sterile barrier for a medical device (e.g., a medical valve or male Luer connector) having an access port prior to first use, and (2) provide a means for tethering a protective cap to the medical device. When it is time to access the medical device through the access port, the protective covering may be removed from the access port, the access port may be accessed (e.g., another medical device may be connected), and the protective cap may be removed from the covering and used to cover and protect the access port. Details of illustrative embodiments are discussed below. It should be noted that, although the figures and embodiments discussed below refer to medical valves and male Luer connectors, various embodiments of the protective covering described herein can be used for other medical devices with access ports.

FIGS. 1A-1C schematically show a multi-purpose protective covering 100 in accordance with some embodiments of the present invention. The protective covering 100 may include a substrate 110 that has a first end 120 and a second end 130, and provides the structure of the covering 100. As mentioned above and as discussed in greater detail below, the substrate 110 may be tethered to a medical valve 210 or other medical device (FIGS. 2A-2B) having an access port 260, and may be secured to a protective cap 160. To that end, the substrate 110 may have a first securing portion 140 and a second securing portion 150.

The first securing portion 140 may be located nearer the first end 120 of the substrate 110 and may be used to secure the protective cap 160 to the substrate 110. For example, the first securing portion 140 may include adhesive 142 to which the protective cap 160 may be secured (e.g., the upper lip 162 of the protective cap 160 may be adhered to the adhesive 142). In some embodiments, the protective cap 160 may be a swab cap that contains a swab material that is preloaded with a cleaning agent. It is important to note that, by securing the swab cap 160 to the substrate 110 such that the interior of the swab cap 160 (e.g., where the swab material and cleaning agent are located) is facing the substrate 110, the substrate 110 can create a seal against the upper lip 162 of the cap 160 and help prevent the swab material and cleaning agent from drying out.

Alternatively, the first securing portion 140 may be bonded to the cap 160 without an adhesive (e.g., the upper lip 162 of the cap 160 may be directly bonded to the substrate 110). For example, the substrate 110 may be comprised of a melt layer that secures the substrate 110 to the cap 160 upon the application of heat to the substrate 110 or through welding of the cap 160 to the substrate 110.

Figure 2B:
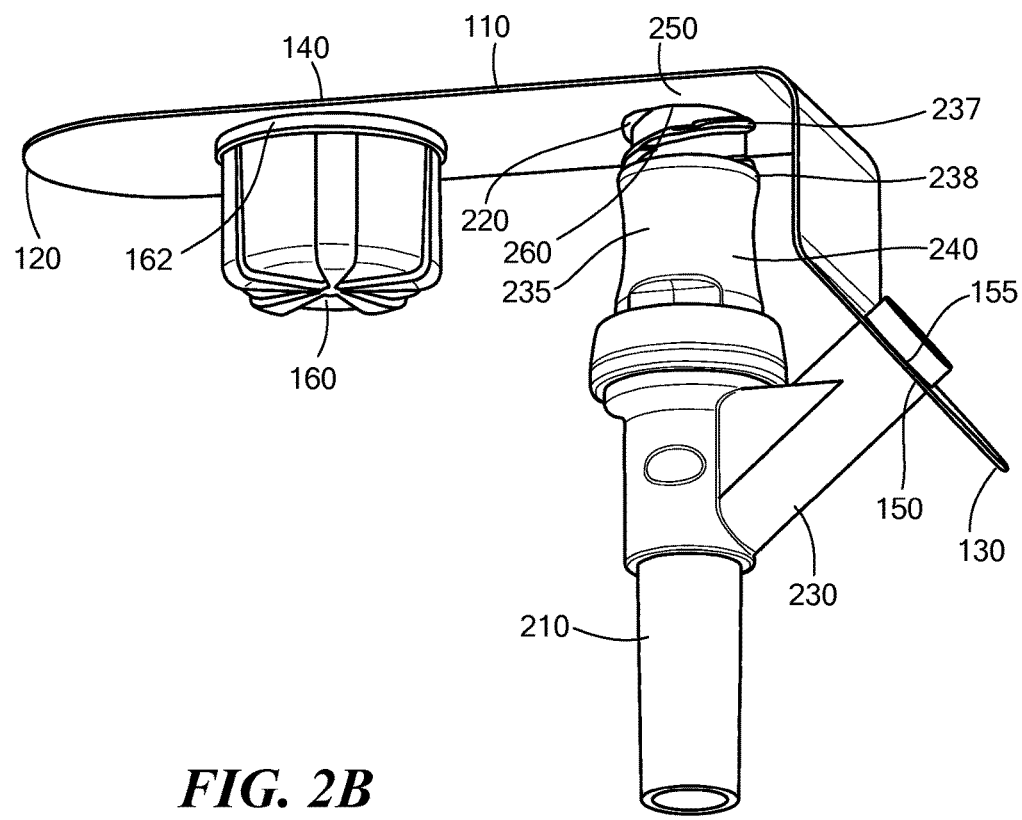

The second securing portion 150 may be located nearer to the second end 130 of the substrate 110. As mentioned above, the second securing portion 150 may be used to tether the substrate 110 (and, thus, the protective cap 160) to the medical valve 210. To that end, the second securing portion 150 may have a through hole 155 passing through the substrate 110. As best shown in FIGS. 2A-2B, this through hole 155 may be used to tether the substrate 110 to the medical valve 210 by inserting an upper outlet 230 of the medical valve 210 (e.g., the Y-site of a medical valve) through the hole 155. Although FIGS. 2A-2B show a medical valve 210 with a Y-site configuration, some embodiments of the present invention may also be used with valves having outlets that are aligned with the valve inlet 220 (e.g., in-line valves). In such embodiments, the outlet may be inserted into the hole 155 in a manner similar to that shown for the Y-site medical valve 210.

As best shown in FIGS. 2A and 2B, the sealing portion 250 may be located between the first and second securing portions 140/150, and can be used to seal the medical valve 210 to the substrate 110. For example, the sealing portion 250 may create a seal between the substrate 110 and the inlet 220 of the medical valve 210. As discussed in greater detail below, the sealing portion 250 and the substrate 110 may create a sterile barrier that maintains the sterility of the access port 260 (e.g., the opening of the inlet 220) prior to the first use of the medical valve 210. Additionally, the substrate 110 can have an antimicrobial coating that helps maintain a degree of sterility at all times, and helps maintain the sterile barrier for the medical valve 210. Like the first securing portion 140, the sealing portion 250 may include an adhesive to secure the substrate 110 to the medical valve 210. Alternatively, the sealing portion 140 may be directly bonded to the medical valve 210 upon the application of heat to the substrate 110 or through welding of the sealing portion 250 to the medical valve 210.

Figure 3A:
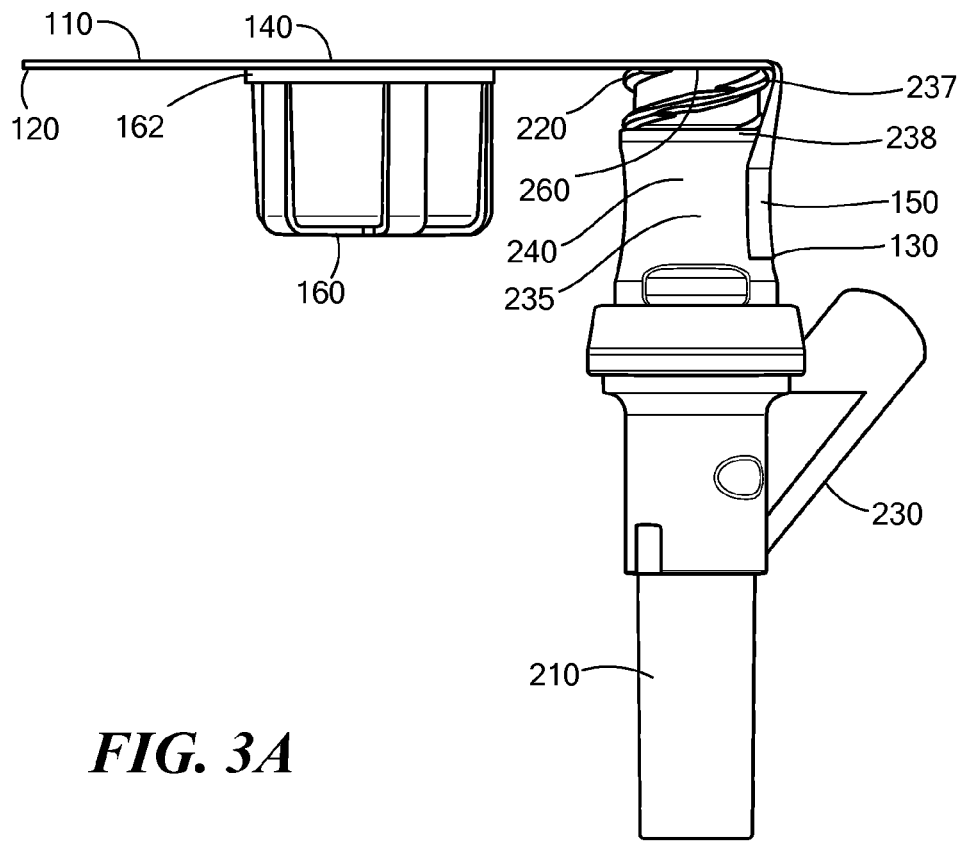
FIGS. 3A-3B schematically show an alternative embodiment of a multi-purpose protective covering secured to a medical valve, in accordance with additional embodiments of the present invention.
Figure 3B:
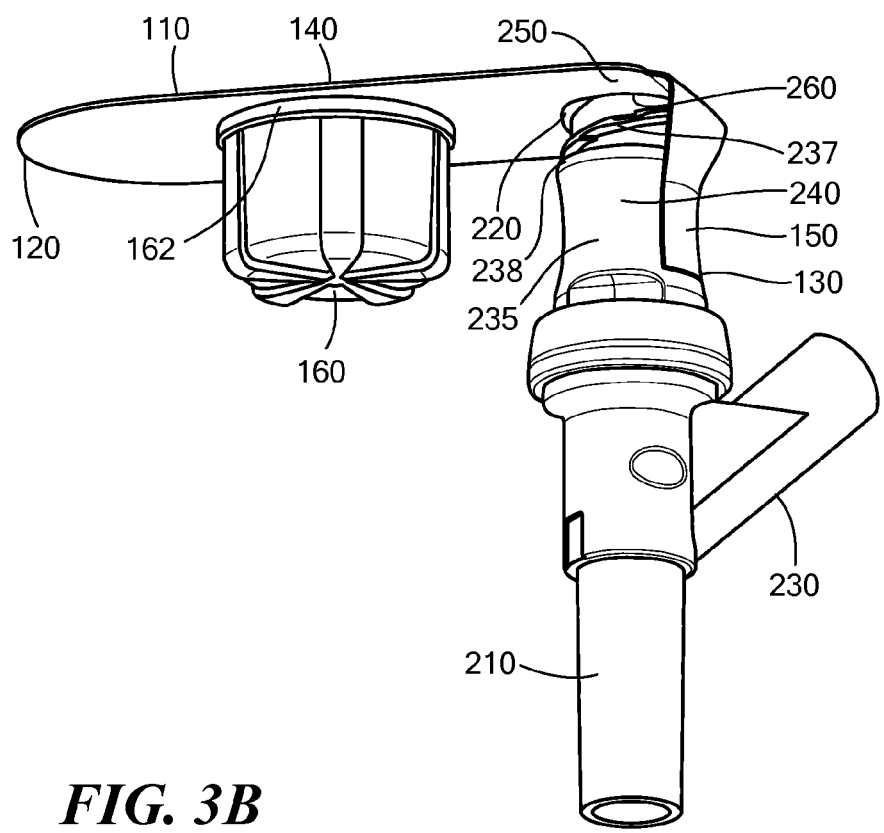

Although, the second securing portion 150 is described above as having a through hole 155 into which the upper outlet 230 of the medical valve 210 may be inserted to tether the valve 210 to the substrate 110, some embodiments can use alternative ways to secure/tether the substrate 110 to the medical valve 210. For example, as shown in FIGS. 3A-3B, the second securing portion 150 may be bonded to a side wall 240 of the medical valve 210 (e.g., a side wall of the inlet housing 235). To that end, instead of a through hole 155, the second securing portion may include an adhesive and/or other adhering agent that secures the second securing portion 150 and, thus, the substrate 110 to the medical valve 210. In such embodiments, the second securing portion 150 may extend all the way to the second end 130 of the substrate 110. Alternatively, the second securing portion 150 may be directly bonded to the medical valve 210 upon the application of heat to the substrate 110 or through welding of the second securing portion 150 to the medical valve 210.

During use, when medical personnel requires a new medical valve 210, they may remove the medical valve 210, substrate 110, and protective cap 160 (which, as discussed in greater detail below, may be packaged together and pre-assembled as a kit) from the sterile packaging, and peel the sealing portion 250 of the substrate 110 away from the medical valve 210 to provide initial access to the inlet 220/access port 260. As discussed above, various embodiments of the present invention create a sterile barrier over the inlet 220 of the valve 210, thereby maintaining the sterility of the access port 260 prior to its first use and/or until the sealing portion 250 is peeled away. Once the medical valve access port 260 is exposed, the medical personnel may connect a male luer to the medical valve 210 (or vice versa if the protective covering is located on the male Luer connector), and transfer fluid through the valve 210 and male Luer connector.

After using the medical valve for the first time and prior to subsequent uses, the medical personnel may disconnect the male Luer connector, and remove the protective cap 160 from the substrate 110 (e.g., by peeling away the first securing portion 140 from the protective cap 160), and use the protective cap 160 to cover the inlet 220 of the medical valve 210. Furthermore, if the protective cap 160 is a swab cap for cleaning the access port 260 per standard practices, the medical personnel can also clean the inlet 220 of the medical valve 210. It is important to note that, because the second securing portion 150 tethers the protective cap 160 to the medical valve 210, the protective cap 160 should be nearby and readily available for use by the medical personnel.

Additionally, depending upon the adhesive used and/or the heat seal process applied to secure the cap 160 to the substrate 110, some embodiments of the present invention may allow the cap 160 to be re-secured to the first securing portion 140. For example, after the medical personnel has finished cleaning the inlet 220 and is ready to connect/reconnect the male luer, they may remove the cap 160 from the valve 210 and re-secure the cap 160 (or secure a new cap 160) to the adhesive 142 on the first securing portion 140. In this manner, the medical personnel can ensure that the protective cap 160 is not lost and/or that a new protective cap 160 is available for future use.

Figure 4A:
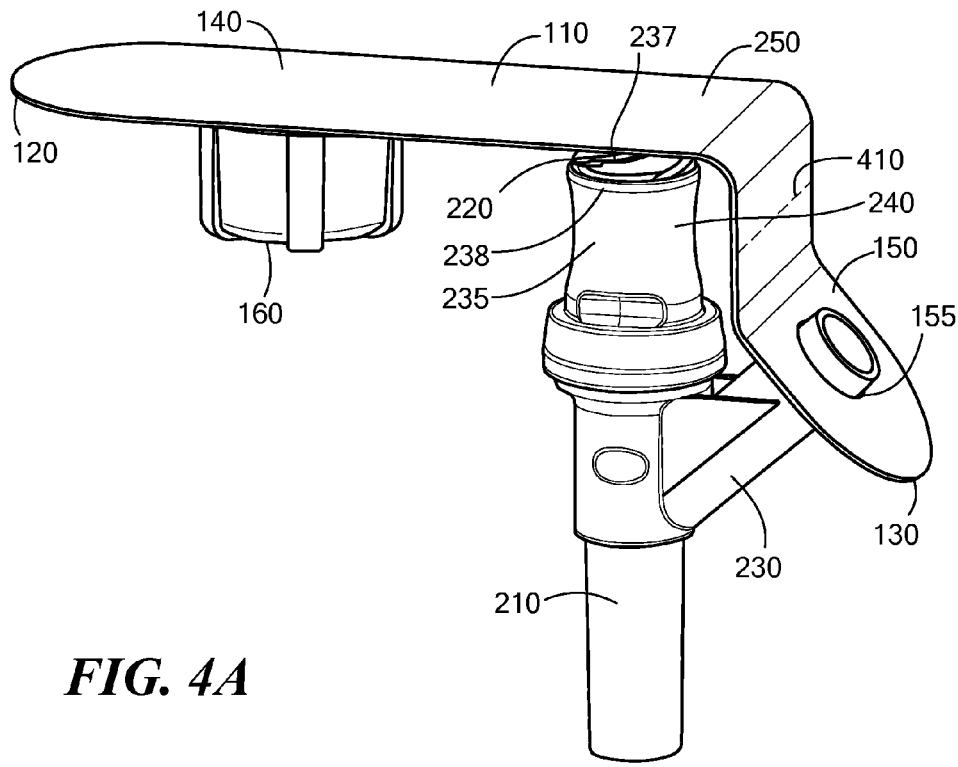
FIGS. 4A-4B schematically show a further alternative embodiment of the multi-purpose protective coating with perforations to help with removal from the medical valve, in accordance with further embodiments of the present invention.
Figure 4B:
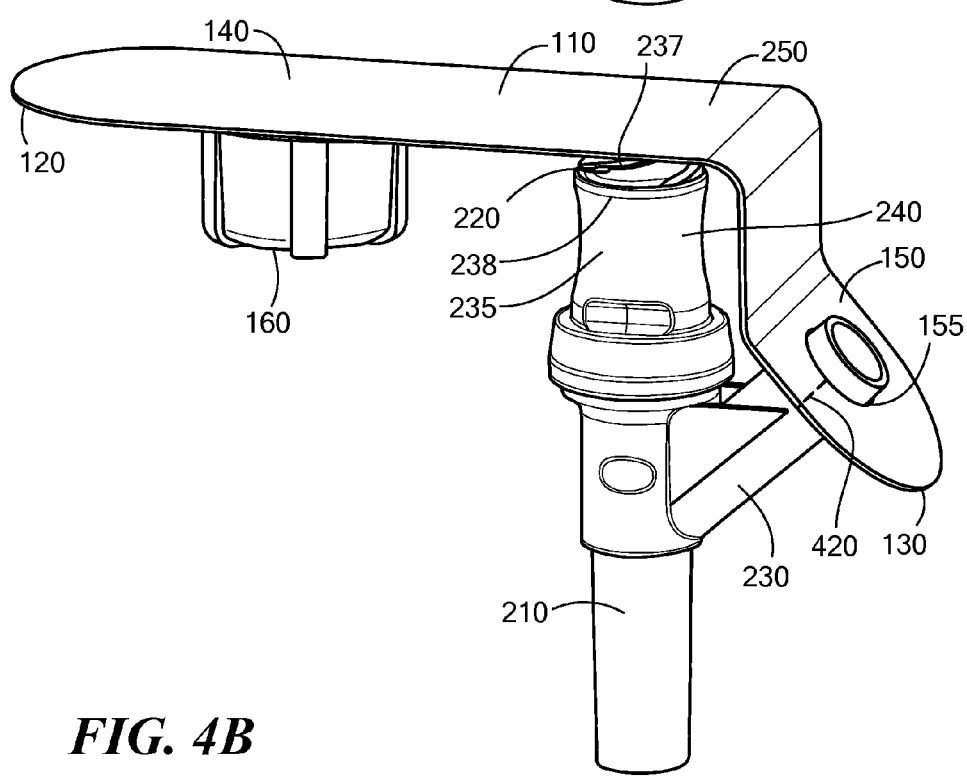

In order to ease removal of the substrate 110 from the medical valve 210 (e.g., to either remove the covering 100 completely or just peel the substrate 110 off of the medical valve), some embodiments of the present invention may have perforations 410 that allow a user to easily tear the substrate 110. For example, as shown in FIG. 4A, the perforations 410 may be located between the second securing portion 150 (e.g., the hole 155) and the sealing portion 250 (FIG. 4A). Additionally or alternatively, the perforations 410 may be located between the hole 155 and the edge 420 of the substrate 110 (FIG. 4B). In embodiments with perforations 410, when a user wishes to remove the substrate 110, they may simply tear the substrate 110 along the perforations 410 and remove the substrate 110. Alternatively, the perforations 410 may be replaced or supplemented by a notch located at the edge 420 of the substrate 110 (not shown) to facilitate tearing of the substrate 110.

Figure 5A:
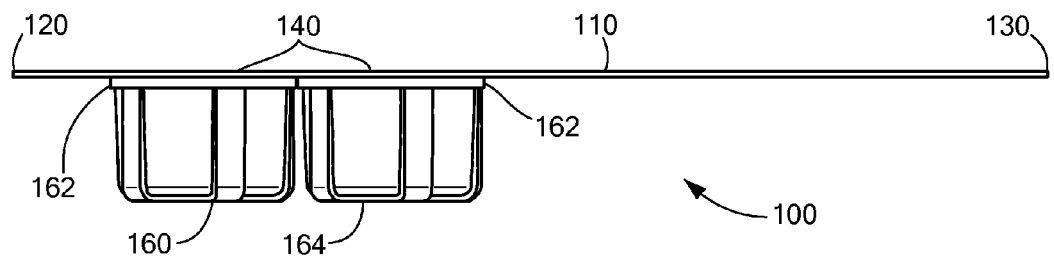
FIGS. 5A-5C schematically show an alternative embodiment of a multi-purpose protective covering, in accordance with embodiments of the present invention.
Figure 5B:
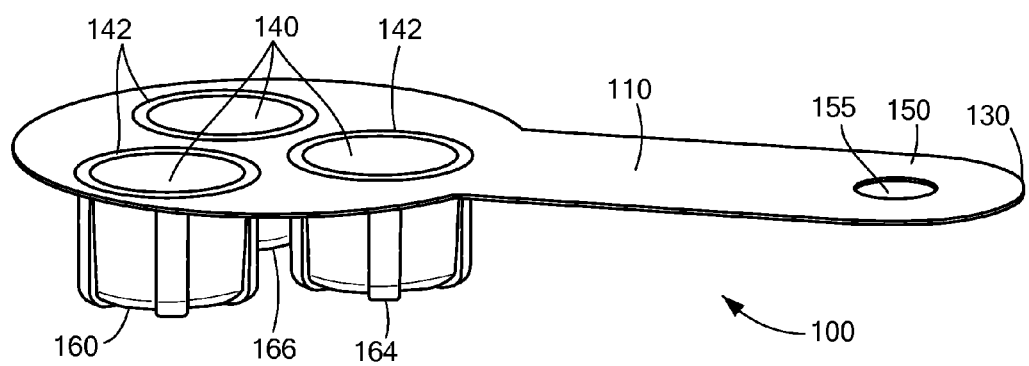
Figure 5C:
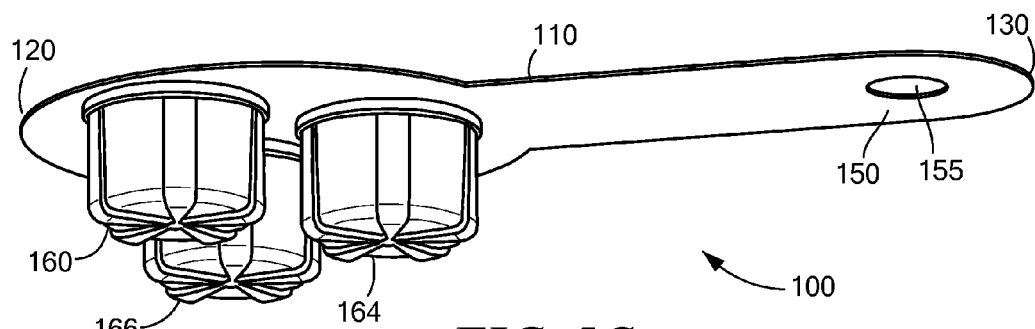

As mentioned above, it is important that a protective cap 160 be available when needed. To that end, as shown in FIGS. 5A-5C, some embodiments can have multiple caps secured to the first securing portion 140. For example, as shown in FIGS. 5A-C, the first securing portion 140 of substrate 110 may include protective caps 160, 164, and 166. It should be noted that, although FIGS. 5A-5C show three caps 160/164/166, other embodiments can have two caps, or more than three caps.

Figure 6B:
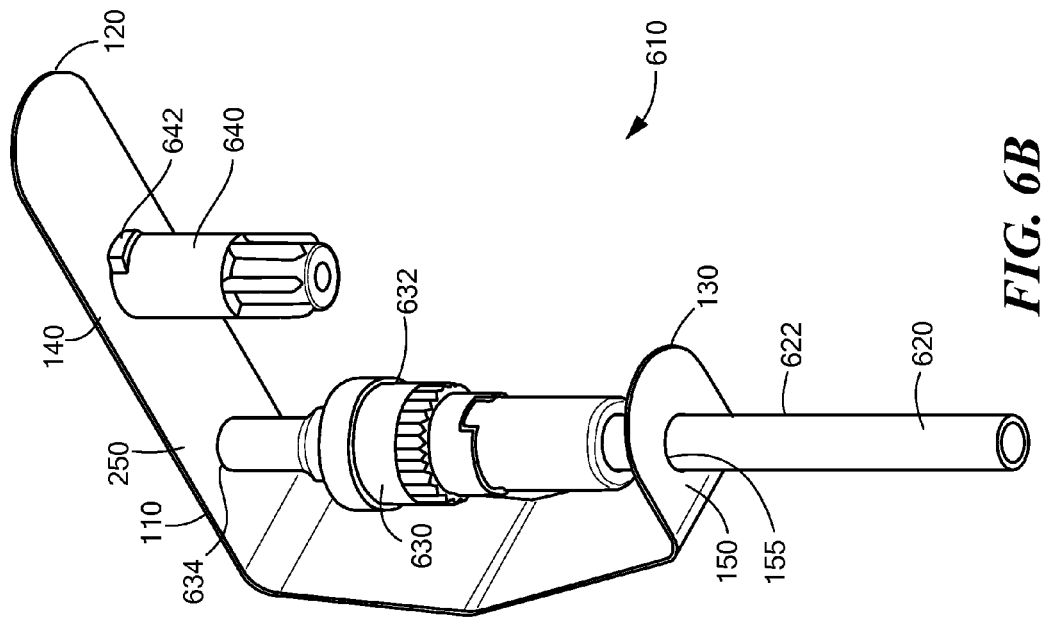
Figure 6A:
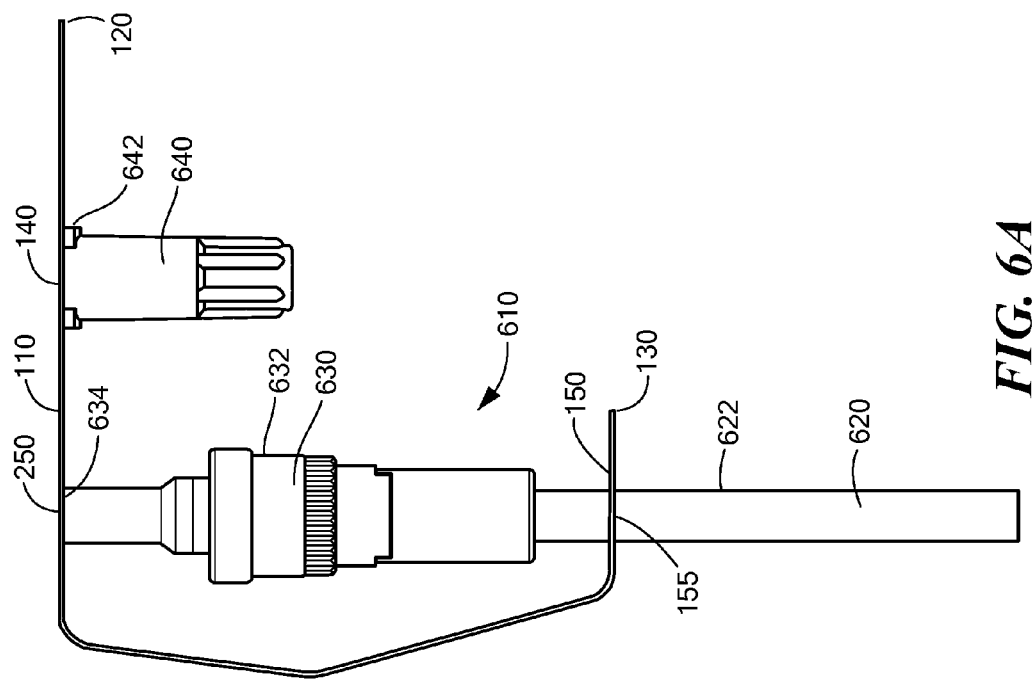

Although the above embodiments describe the substrate 110 as being secured to the medical valve 210, as mentioned above, other embodiments of the present invention may be secured to other medical devices. For example, some embodiments may be secured to a male Luer connector 630 within an IV set 610 to which the medical valve 210 is connected to just prior to use. In such embodiments, as shown in FIGS. 6A to 6C, the second securing portion 150 of the protective covering 100 (e.g., the substrate 110) can be secured to the IV set 610 (e.g., the tubing 620 of the IV set or the male Luer connector 630 on the IV set 610). Like the embodiments described above, the second securing portion 150 may include a through hole 155 passing through the substrate 110. As shown in FIG. 6A-6C, the IV set 610 may be threaded through this through hole 155 such that the substrate 110 is tethered to the IV set 610.

Alternatively, the second securing portion 150 may be bonded to a side wall 622 of the IV set tubing 620 and/or or a side wall 632 of the male Luer connector 630. For example, the second securing portion 150 may include an adhesive and/or other adhering agent that secures the second securing portion 150 to the IV set 610 (e.g., to either the tubing 620 or the male Luer connector 630). The second securing portion may also be directly bonded to the tubing 620 and/or male Luer connector 630 upon application of heat to the substrate 110 and/or through welding of the substrate 110 to the IV set 610.

Like the above described embodiments, the sealing portion 250 may also be located between the first and second securing portions 140/150, and may be used to seal the male Luer connector 630 to the substrate 110. For example, the sealing portion 250 may create a seal between the substrate 110 and a port 634 of the male Luer connector 630 (e.g., the portion of the male Luer connector 630 that is inserted into/connected with the medical valve 210 to actuate the valve 210). The sealing portion 250 and the substrate 110 create a sterile barrier that maintains the sterility of the port 634 (and therefore, the male Luer connector 630 and IV set 610) prior to the first use of the IV set 610. The sealing portion 250 may include an adhesive to secure the substrate 110 to the male Luer connector 630. Alternatively, the sealing portion 250 may be directly bonded to the male Luer connector 630 upon application of heat to the substrate 110 or through welding of the male Luer connector 630 to the substrate 110.

Although the embodiments described above include a protective cap 160 for the medical valve 210, other embodiments can include different protective caps. To that end, as also shown in FIGS. 6A-6C, some embodiments can include a protective cap 640 for the male Luer connector 630. The male Luer cap 640 can be secured to the first securing portion 140 of the covering 100 in a manner similar to that of the medical valve cap 160. For example, the first securing portion 140 can include an adhesive to which the male Luer cap 640 may be secured (e.g., the upper lip 642 of the male Luer cap 640 may be adhered to the adhesive). Alternatively, the first securing portion 140 may be bonded to the male Luer cap 640 without an adhesive (e.g., the upper lip 642 may be directly bonded to the substrate 110) upon application of heat to the substrate 110, and/or by welding the substrate 110 to the cap 640.

Like the valve cap 160, the male Luer cap 640 can be a swab cap that contains a swab material that is preloaded with a cleaning agent. To prevent the swab material and cleaning agent from drying out, it is important to note that the interior of the male Luer cap 640 should face the substrate 110 when secured. The substrate 110 may then create a seal against the male Luer cap 640 (e.g., the upper lip 642) to prevent air from drying out the swab material. In a manner similar to the valve cap 160, after the first use of the male Luer connector 630, the male Luer cap 640 may be removed from the substrate 110 and used to clean and cover the port 634 of the male Luer connector 630.

Figure 7C:
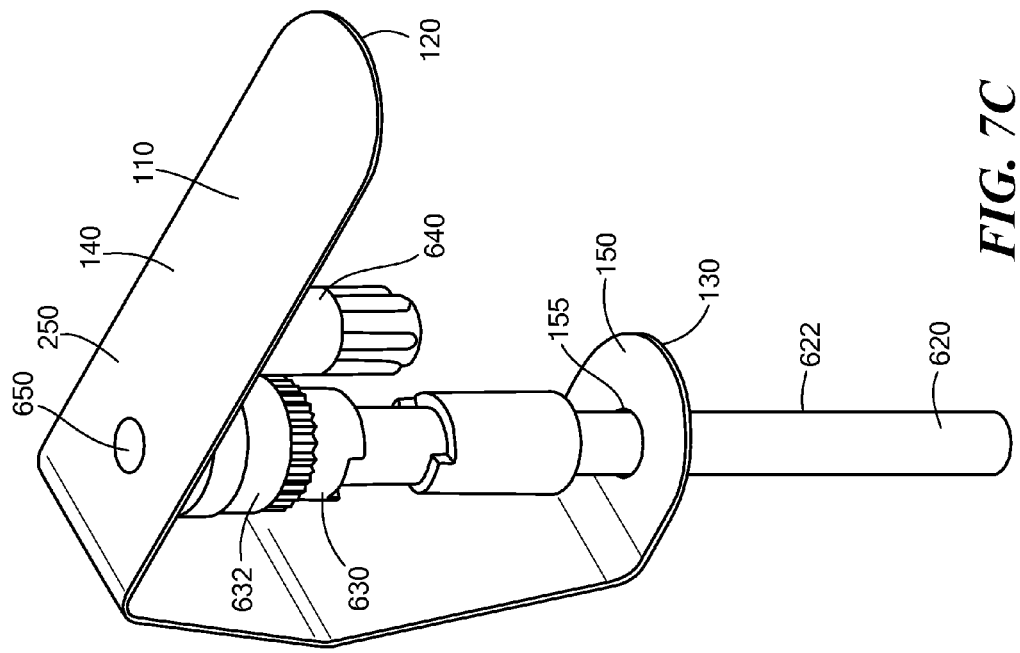
Figure 7B:
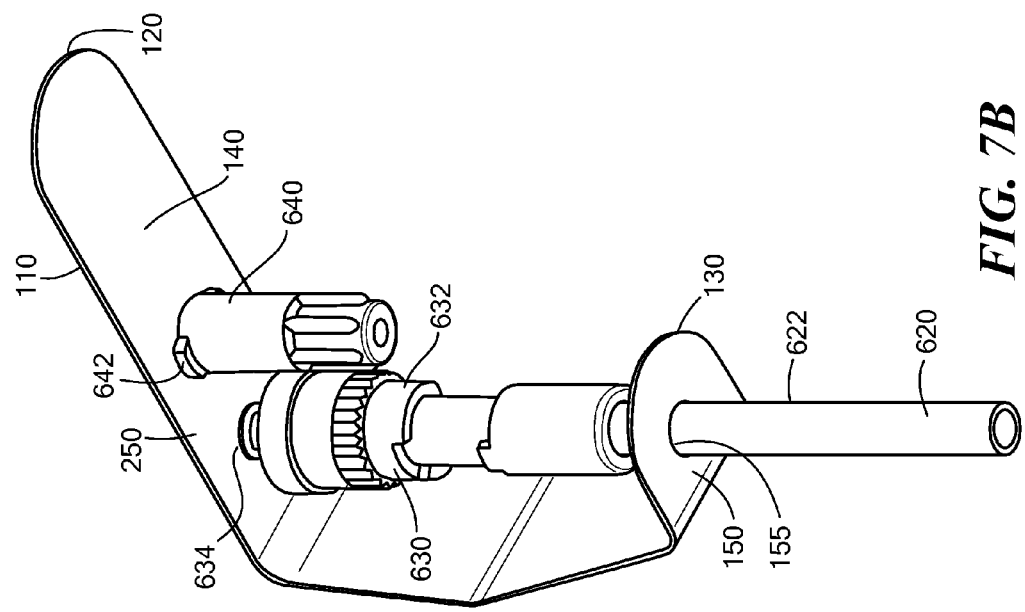

As shown in FIGS. 7A-7C, in some embodiments, the covering 110 can include a hydrophobic filter 650 located within the sealing portion 250. For example, when the substrate 110 is sealed over the male Luer connector 630, the filter 650 may be located over the port 634 (e.g., the access port) within the male Luer connector 630. The filter 650 allows air within the tubing 620 of the IV set 610 to escape, but prevents bacteria and other contamination from entering the IV set 610 through the port 634 on the male Luer connector 630. To that end, the filter 650 allows a user to prime the IV set 610 (e.g., the tubing 620) without removing the covering 100 and risking contaminating the IV set 610. For example, as the user primes the IV set 610 (e.g., with saline solution, medicine, etc.), the priming solution will cause air within the IV set 610 to be pushed out of the tubing 620 and male Luer connector 630 through the filter 650. However, because the filter 650 is hydrophobic, the filter 650 prevents the priming solution from passing. Additionally, the filter 650 will prevent external bacteria from entering the male Luer connector 630 and IV set 610.

Figure 8B:
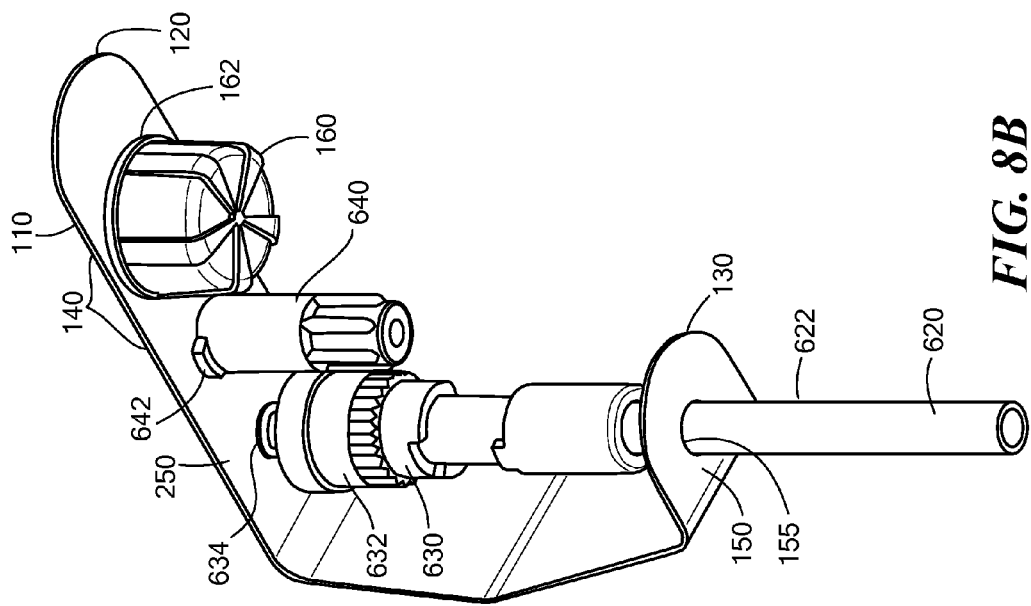
FIGS. 8A-8C schematically show a further alternative embodiment of a multi-purpose protective covering having multiple types of protective caps, in accordance with embodiments of the present invention.
Figure 8A:
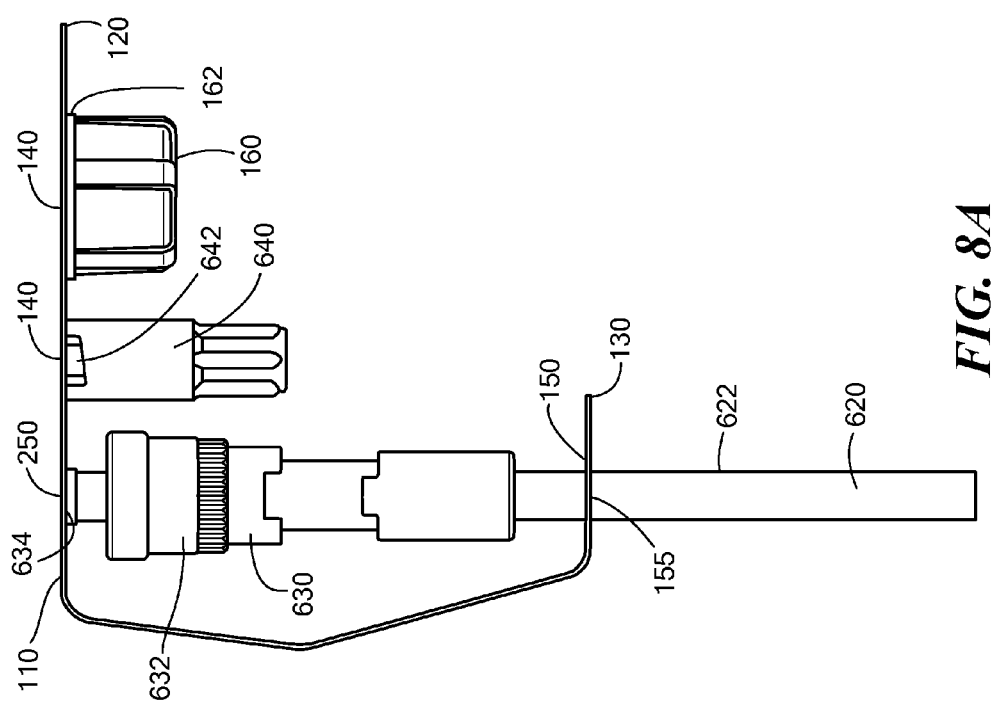
Figure 8C:
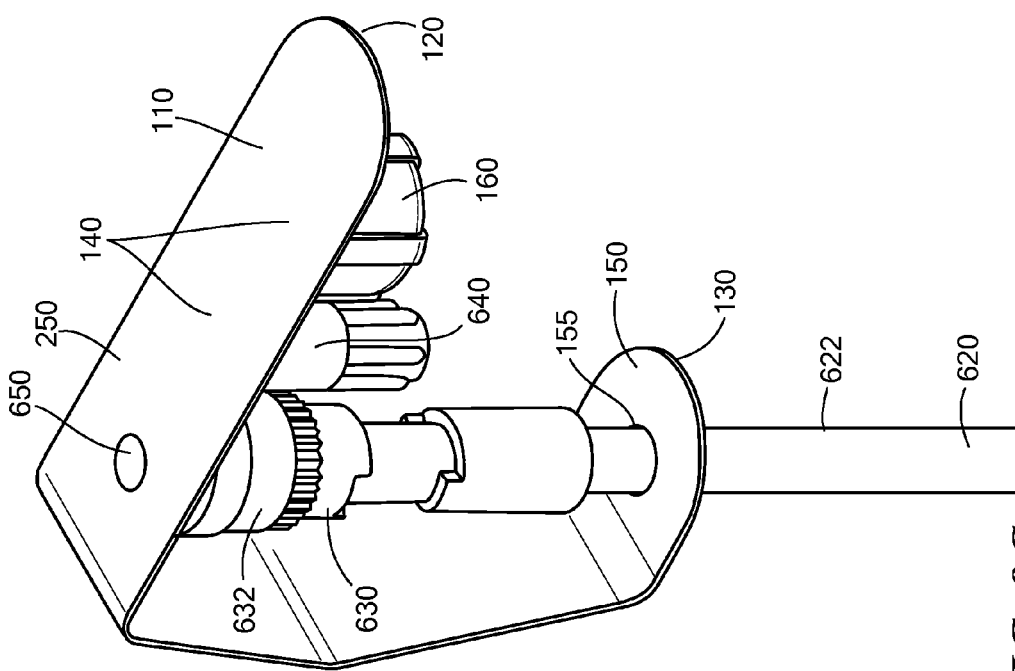

Although the embodiments discussed above include one or more protective caps 160/640 for the medical device on which the covering 100 is attached (e.g., the covering 100 secured to the medical valve 210 includes one or more protective caps 160 for the medical valve 210, and the covering 100 secured to the IV set 610 has one or more protective caps 640 for the male Luer connector 630), some embodiments may include caps for both the medical valve 210 and the male Luer connector 630, regardless of which medical device the covering 100 is attached to. For example, as shown in FIGS. 8A-8C, the covering 100 may be secured/tethered to the IV set 610, and may include both a male Luer cap 640 and a medical valve cap 160. Alternatively, the covering 100 may be secured to the medical valve 210 and include both a male Luer cap 640 and a medical valve cap 160. In this manner, a protective covering 100 need not be secured/tethered to both the medical valve 210 and the IV set 610, and various embodiments help ensure that the medical personnel has caps for both medical devices when needed.

Figure 9A:
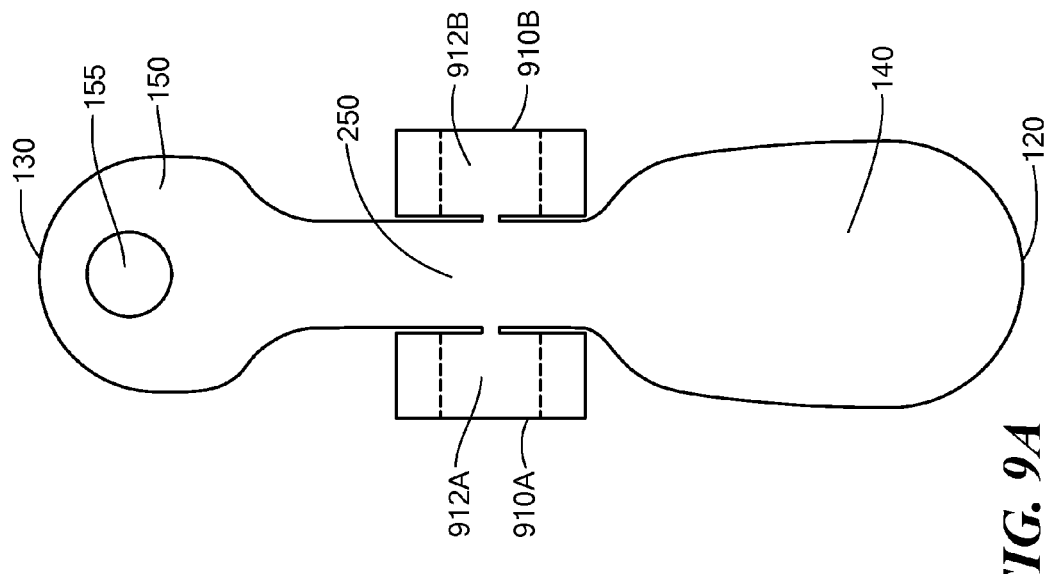

In order to provide additional protection for the medical devices, some embodiments of the protective covering 100 can have additional features that cover a portion of the housing of the medical device (e.g., in addition to the access port). To that end, as shown in FIGS. 9A-9C, some embodiments of the present invention can include one or more tabs 910A/B connected to and extending outward from the sealing portion 250 of the protective covering 100. For example, as best shown in FIG. 9A, the tabs 910A/B may be connected to the sealing portion 250 via a narrow "bridge" of material that extends from the sealing portion 250 and allows the tabs 910A/B to be easily folded down and wrapped around a portion of the housing.

To further protect the medical device (e.g., the medical valve 210 shown in FIGS. 9A-9C or the male Luer connector 630), once the protective covering 100 is applied to the medical valve 210 (e.g., once the sealing portion 250 is secured to/sealed against the access port 260), the tabs 910A/B may be folded down towards the medical valve 210 and wrapped around the inlet housing 235. In some embodiments the underside 912A/B of the tabs 910A/B (e.g., the surface that faces the medical device 210 when the tabs 910A/B are folded down) may include an adhesive to allow the tabs 910A/B to adhere to the inlet housing 235 of the medical valve 210, and/or to each other as the tabs 910A/B are wrapped around the inlet housing 235. Alternatively, the tabs 910A/B can be bonded to one another and/or to the inlet housing 235 in any of the manners described above (e.g., welding, heat, energy, etc.).

In this manner, the tabs 910A/B can provide additional protection against damage and/or contamination. For example, if the medical device is a medical valve 210 (e.g., as shown in FIGS. 9A-9C), the tabs 910A/B may be wrapped around the threads 237 on the inlet housing 235 (e.g., the threads used to connect a male Luer connector) to protect the threads 237 (and the inlet housing 235) from damage and contamination prior to the first use of the valve. During use, when medical personnel requires a new medical valve 210, they may peel away the sealing portion 250 of the substrate 110 and the tabs 910A/B from the medical valve 210 to provide initial access to the inlet 220 and the threads 237 on the inlet housing 235.

Figure 10C:
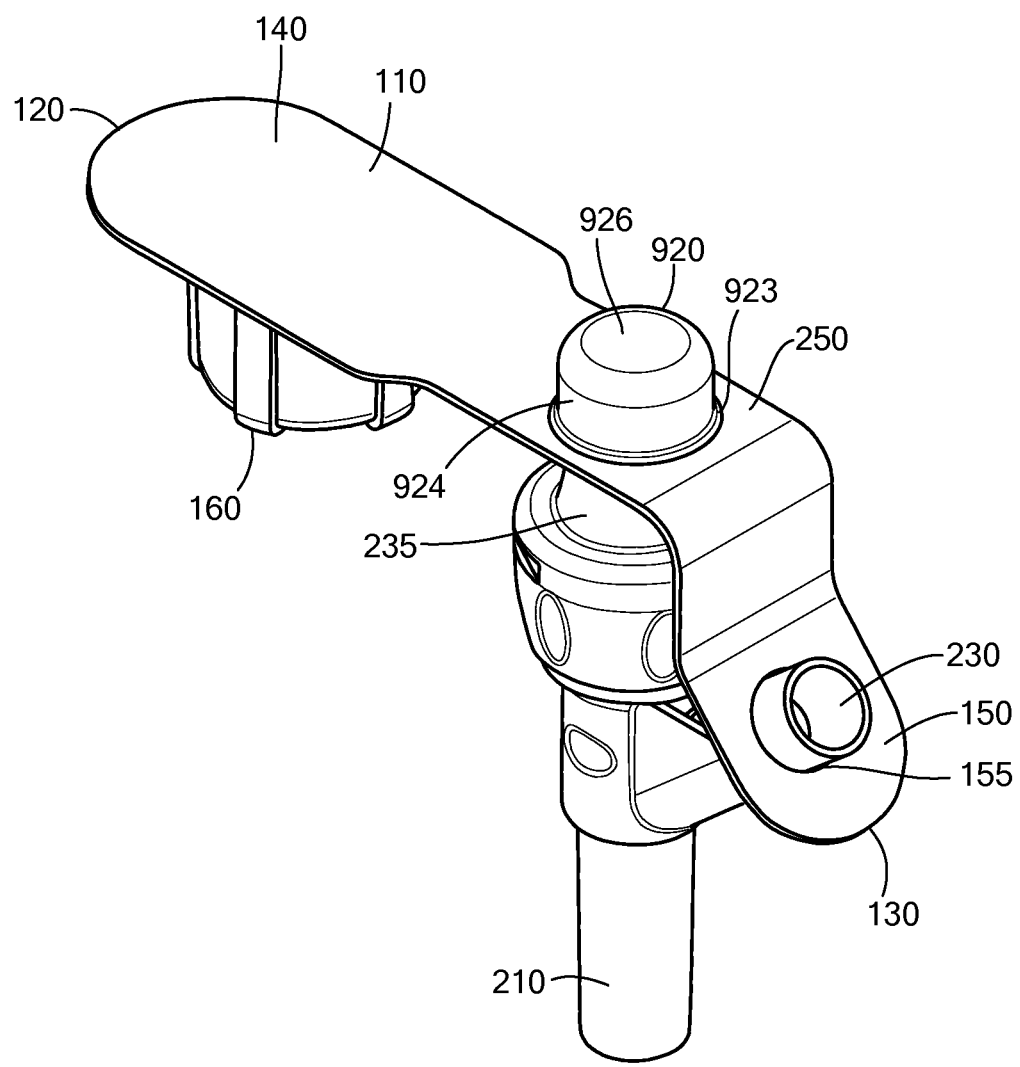

Instead of the tabs 910A/B described above, some embodiments may have alternative features to help protect the medical device 210. For example, as shown in FIGS. 10A-10C, the protective covering 100 may be formed with a blister (e.g., a pocket 920) having an annular wall 924 that extends upward from the top surface of the protective covering 100 (e.g., from the sealing portion 250 of the substrate 110), and forms an interior cavity 922. In such embodiments, the protective covering 100 may be placed on the medical valve (or other medical device) such that a portion of the inlet housing 235 and the threads 237 sit within the interior cavity 922, and the access port is covered by a top surface 926 of the pocket 920 (FIGS. 10B and 10C).

Once the pocket 920 is in place over the inlet housing 235 of the medical valve 210, it may be sealed to medical valve 210 using any of the techniques described above (e.g., adhesive, heat, welding, etc.). For example, the lower portion 923 of the annular side wall 924 of the pocket 920 may be sealed to the side of the medical valve 210 (e.g., to the side of the inlet housing 235), to the threads 237 on the inlet housing 235, or, if the valve 210 is so equipped, to a shoulder 238 located just below the threads 237. In some embodiments (e.g., particularly those in which the pocket 920 is sealed against the shoulder 238), the seal between the pocket 920 and the medical valve 210 will create a sterile barrier that will prevent contamination from entering the interior cavity 922 of the pocket 920, and thus the interior of the medical valve 210 via the port 260.

It is important to note that, in addition to the seal between the lower portion 923 of the side wall 924 of the pocket 920 and the medical valve 210 (or instead of in those embodiments in which the seal does not create a sterile barrier), there may also be a seal around the periphery of the access port of the medical device (e.g., the medical valve port 260 or the male Luer port 634). For example, the top surface 926 of the pocket 920 may include an adhesive to seal to the periphery of the access port. Additionally or alternatively, the top surface 926 may be sealed to the periphery of the access port (e.g., the medical valve port 260 or the male Luer port 624) using any of the techniques described above (e.g., welding, heat sealing, etc.).

Each of the above described embodiments can be packaged and sold as a kit. The kit may include the medical valve 210 (or the IV set 610), the substrate 110, and the protective cap(s) 160/162/164/640. In some embodiments of the kit, the components may come pre-assembled (e.g., the substrate 110 may be tethered to the medical valve 210 via the second securing portion 150, the medical valve 210 may be sealed to the sealing portion 250, and the protective cap 160 may be secured to the first securing portion 140).

Although the above discussion discloses various exemplary embodiments of the invention, it should be apparent that those skilled in the art can make various modifications that will achieve some of the advantages of the invention without departing from the true scope of the invention.

What is claimed is:

1. A multi-purpose covering for use with a medical device having a housing and an access port, the multi-purpose covering comprising: a substrate having a first end and a second end and defining the structure of the covering; a first securing portion nearer the first end of the substrate configured to removably secure at least one protective cap to the substrate, the at least one protective cap having an opening that is sealed by the substrate prior to removing the at least one protective cap; a second securing portion nearer the second end securing the substrate to the medical device; and a sealing portion of the substrate releasably sealing the access port prior to first use of the medical device, the at least one protective cap configured to be placed on the access port after removal of the sealing portion.

2. A covering according to claim 1, wherein the sealing portion is located between the first securing portion and the second securing portion.

3. A covering according to claim 1, wherein the first securing portion has an adhesive, the adhesive securing the substrate to the at least one protective cap.

4. A covering according to claim 1, wherein the first securing portion is bonded to the at least one protective cap.

5. A covering according to claim 1, wherein the sealing portion includes an adhesive for sealing the sealing portion to the medical device.

6. A covering according to claim 1, wherein the sealing portion is bonded to the medical device.

7. A covering according to claim 1, wherein the second securing portion includes a through hole passing through the substrate, the through hole fitting over at least a portion of the medical device, thereby securing the substrate to the medical device.

8. A covering according to claim 1, wherein the second securing portion is bonded to at least a portion of the medical device.

9. A covering according to claim 1, wherein the second securing portion includes an adhesive, the adhesive securing the substrate to the medical device.

10. A covering according to claim 1, wherein the at least one protective cap contains a swab material pre-loaded with a cleaning agent.

11. A covering according to claim 1, wherein the at least one protective cap includes at least one medical valve protective cap and at least one male Luer protective cap.

12. A covering according to claim 1, wherein the sealing portion is welded to the medical device.

13. A covering according to claim 1, wherein the first securing portion is welded to the at least one protective cap.

14. A covering according to claim 1, wherein the second securing portion is welded to at least a portion of the medical device.

15. A covering according to claim 1, further comprising at least one protective cap.

\* \* \* \* \*